(12) United States Patent
Lenouvel et al.

(10) Patent No.: US 8,859,269 B2
(45) Date of Patent: Oct. 14, 2014

(54) CHEMICAL ACTIVATION OF AN ACTUATOR OR AN OSMOTIC MOTOR

(75) Inventors: François Lenouvel, Grenoble (FR); Vanessa Durrieu, Saint Etienne de Fontbellon (FR); Naceur Belgacem, Brie et Angonnes (FR); Philippe Cinquin, Saint Nazaire les Eymes (FR)

(73) Assignees: Universite Joseph Fourier, Grenoble (FR); Institut National Polytechnique de Grenoble, Grenoble (FR)

( * ) Notice: Subject to any disclaimer, the term of this patent is extended or adjusted under 35 U.S.C. 154(b) by 1898 days.

(21) Appl. No.: 11/883,214

(22) PCT Filed: Feb. 2, 2006

(86) PCT No.: PCT/FR2006/050092
§ 371 (c)(1),
(2), (4) Date: May 16, 2008

(87) PCT Pub. No.: WO2006/082345
PCT Pub. Date: Aug. 10, 2006

(65) Prior Publication Data
US 2009/0120082 A1    May 14, 2009

(30) Foreign Application Priority Data

Feb. 3, 2005 (FR) ..................... 05 50314

(51) Int. Cl.
  *C12M 1/00* (2006.01)
  *F03G 7/00* (2006.01)
  *F04B 17/00* (2006.01)
  *F04B 43/02* (2006.01)
  *A61M 1/12* (2006.01)

(52) U.S. Cl.
  CPC ................ *F03G 7/005* (2013.01); *F04B 17/00* (2013.01); *F04B 43/02* (2013.01); *A61M 1/127* (2013.01)

USPC ................ 435/289.1; 435/252.3; 435/283.1; 435/287.4; 60/325

(58) Field of Classification Search
  CPC .......... F03G 7/005; F04B 43/02; F04B 17/00; A61M 1/127
  USPC ............ 60/325; 435/252, 283.1, 287.4, 289.1
  See application file for complete search history.

(56) References Cited

U.S. PATENT DOCUMENTS

| | | | |
|---|---|---|---|
| 3,587,227 A * | 6/1971 | Weingarten | 60/326 |
| 3,894,538 A | 7/1975 | Richter | |
| 4,522,698 A | 6/1985 | Maget | |
| 2005/0158841 A1 * | 7/2005 | Cinquin et al. | 435/252.3 |

FOREIGN PATENT DOCUMENTS

WO    WO 03/072941    9/2003

OTHER PUBLICATIONS

International Search Report dated Jun. 12, 2006 (2 pgs.).

* cited by examiner

*Primary Examiner* — Michael Hobbs
(74) *Attorney, Agent, or Firm* — Howard IP Law Group, PC (57) ABSTRACT

An actuator that includes an enclosure having a wall impermeable to a first solute and permeable to a solvent and containing, at least temporarily, a catalyst capable of promoting the transformation of at least one second solute into the first solute to vary the osmotic pressure in the enclosure; and a deformable chamber connected to the enclosure, the chamber being capable of increasing in volume under the action of the solvent moving from the enclosure into the chamber by osmosis or the enclosure being designed to be arranged in contact with the solvent, the chamber being capable of increasing in volume under the action of the solvent penetrating into the enclosure by osmosis.

15 Claims, 4 Drawing Sheets

CHEMICAL ACTIVATION OF AN ACTUATOR OR AN OSMOTIC MOTOR

This application claims the benefit of French Application No. 05/50314, filed Feb. 3, 2005 and Intl. Application No. PCT/FR2006/050092, filed Feb. 2, 2006, the entire disclosures of which are incorporated herein by reference.

BACKGROUND OF THE INVENTION

1. Field of the Invention

The present invention relates to devices that can be used as actuators or as motors which are easy to form, which use low-cost fuel, and which emit little or no waste.

Further, the present invention relates to devices which can be used as actuators or as motors capable of operating within a biological medium such as the human body or an animal body.

Such actuators and such motors find applications in the medical field, for example, to overcome the impairment of a natural muscle. Muscles that can be replaced or assisted, temporarily or definitively are, for example, the heart muscle, the respiratory muscles, the sphincters, and smooth or striated muscles, in particular skeletal muscles.

Such actuators and such motors also find applications in fields other than the medical field. In particular, such a motor may be used in all fields where a low waste generation is an important factor in selecting the motor. It may be, for example, the automobile field where the polluting waste generated by the motor used to drive the vehicle wheels is desired to be decreased as much as possible.

2. Discussion of the Related Art

US patent application 2004/248269 of the applicant describes an osmotic actuator intended to be dipped in a biological medium and comprising a deformable enclosure having a semi-permeable membrane, the enclosure containing a solute likely to be osmotically active.

Patent application EP-A-1481165 of the applicant describes an actuator and an osmotic motor with an operation that can be controlled with more accuracy. For this purpose, patent application EP-A-1481165 provides use of microorganisms which are contained in an enclosure permeable to a solvent and impermeable to a first solute. The microorganisms are capable of transforming a second solute into the first solute. A deformable chamber is connected to the enclosure and can see its volume increase under the action of the solvent penetrating into the enclosure by osmosis as the microorganisms are providing the first solute.

A disadvantage of such an actuator and of such an osmotic motor is that keeping microorganisms alive imposes constraining conditions of use. More specifically, it is necessary to dissolve, in the solvent in which the microorganisms are arranged, substances essential to the metabolism of the microorganisms, for example, glucose and oxygen. It is further necessary to provide the discharge of the waste generated by the cellular metabolism, especially the carbon dioxide. Further, it is necessary to maintain many parameters such as temperature or the pH of the solvent in which the microorganisms are arranged within generally very small ranges out of which microorganisms cannot survive.

SUMMARY OF THE INVENTION

The present invention aims at an actuator and an osmotic motor with a simplified implementation.

The present invention also aims at an actuator and an osmotic motor that can operate over a long time period without any constraining maintenance operation.

The present invention aims at using, instead of the microorganisms provided in European patent application EP 1481165, one or several catalysts capable of promoting a reaction of transformation of a compound into another compound. Such catalysts may for example correspond to enzymes which are proteins endowed with a very high catalytic power. As compared with patent application EP-A-1481165, the present invention is characterized in a greater room for maneuver as to the conditions of use of the actuator and of the osmotic motor. Indeed, catalysts being non-living compounds, the constraints aiming at ensuring their integrity are less restrictive than those aiming at the survival of microorganisms.

More specifically, the present invention provides an actuator comprising an enclosure having a wall impermeable to a first solute and permeable to a solvent and containing, at least temporarily, a catalyst capable of promoting the transformation of at least one second solute into the first solute to vary the osmotic pressure in the enclosure; and a deformable chamber connected to the enclosure, said chambre being capable of increasing in volume under the action of the solvent moving from the enclosure into the chamber by osmosis or said enclosure being designed to be arranged in contact with the solvent, said chamber being capable of increasing in volume under the action of the solvent penetrating into the enclosure by osmosis.

According to an embodiment of the present invention, said wall of the enclosure is permeable to the second solute.

According to an embodiment of the present invention, said wall of the enclosure is impermeable to the second solute, the catalyst being capable of promoting the transformation of a number of particles of the second solute into a greater or smaller number of particles of the first solute.

The present invention also provides a motor comprising an actuator such as previously described, in which the chamber comprises return means which oppose to the volume increase of the chamber and controllable means for lowering the osmotic pressure in the chamber.

According to an embodiment of the present invention, the wall of the enclosure is impermeable to the second solute, the catalyst being capable of promoting the transformation of a number of particles of the second solute into a greater number of particles of the first solute. The motor further comprises an additional enclosure having a wall permeable to the solvent and impermeable to the first and second solutes and containing an additional catalyst capable of promoting the transformation of a number of particles of the first solute into a smaller number of particles of the second solute, said additional enclosure being connected to the chamber by a valve.

According to an embodiment of the present invention, the wall of the enclosure is impermeable to the second solute, the catalyst being capable of promoting the transformation of a number of particles of the second solute into a greater number of particles of the first solute. The enclosure is arranged in a deformable envelope containing the solvent and the first solute, the enclosure containing an additional catalyst capable of promoting the transformation of a number of particles of the first solute into a smaller number of particles of the second solute, the means for lowering the osmotic pressure in the chamber being a valve capable of connecting up the chamber and the envelope.

The present invention also provides a motor comprising an actuator such as previously described, in which the enclosure is at least partly deformable and is connected to the chamber at the level of the wall. The motor comprises first means for supplying the catalyst into the enclosure, and second means for supplying an additional catalyst, capable of promoting the transformation of the first solute into the second solute, into the enclosure.

According to an embodiment of the present invention, the wall is permeable to the second solute. The catalyst is capable of promoting the transformation of a number of particles of the second solute into a smaller number of particles of the first solute and the additional catalyst is capable of promoting the transformation of a number of particles of the first solute into a greater number of particles of the second solute.

According to an embodiment of the present invention, the second solute is a compound comprising an amine function, the first solute being a complex of the second solute and of an additional solute comprising an aldehyde function, the wall being impermeable to the additional solute. Further, the catalyst is the hydrogen ion, the additional catalyst being the hydroxyl ion.

According to an embodiment of the present invention, the first supply means comprise an additional enclosure designed to receive a solvent containing glucose, the additional enclosure containing glucose oxidase enzymes capable of promoting the oxidation of glucose to provide gluconate ions and hydrogen ions.

According to an embodiment of the present invention, the second supply means comprise an additional enclosure designed to receive a solvent containing urea, the additional enclosure containing urease enzymes capable of promoting the oxidation of urea to provide ammonium ions and carbon dioxide.

The present invention also provides a solution with an osmolarity which is variable according to the pH comprising a first substance having an amine function and a second substance having an aldehyde function.

According to an embodiment of the present invention, the first substance is urea and the second substance is vanillin.

According to an embodiment of the present invention, the second substance is a derivative of vanillin.

The foregoing and other objects, features, and advantages of the present invention will be discussed in detail in the following non-limiting description of specific embodiments in connection with the accompanying drawings.

DETAILED DESCRIPTION

Figure 1A:
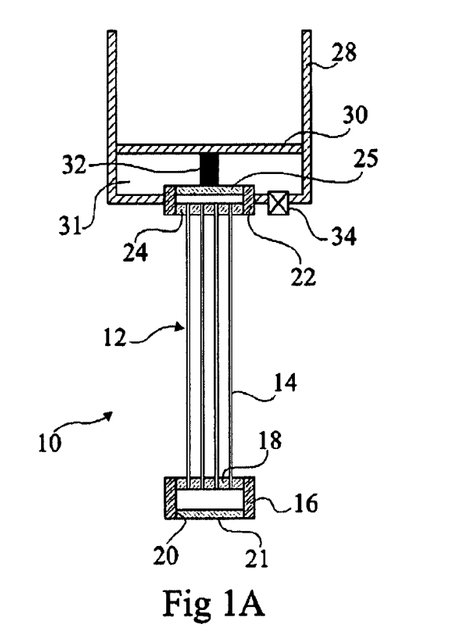
FIGS. 1A and 1B show two steps of the operation of a first embodiment of a motor according to the present invention.
Figure 1B:
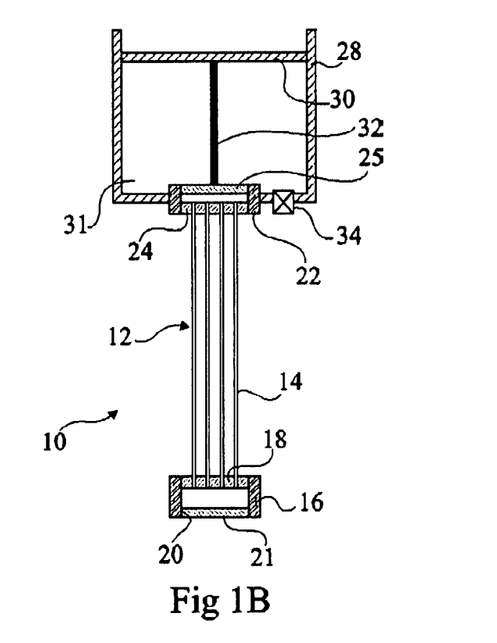

In FIGS. 1A and 1B, an osmotic motor 10 according to the present invention comprises an enclosure 12 formed by a bundle of hollow fibers with semi-permeable walls 14, for example of the type used for dialysis operations. The wall of fibers 14 has a given cut-off threshold, for example, on the order of 200 daltons, that is, it lets through particles having a molecular mass substantially smaller than 200 daltons, that is, than 200 g/mol. Each fiber has, for example, a diameter on the order of 200 μm. Fiber bundle 14 is maintained at a first end by a first junction ring 16, for example, via a gluing area 18. Ring 16 comprises an opening 20 closed by a plug 21. The second end of fiber bundle 14 is maintained by a second junction ring 22, for example, via a gluing area 24. A membrane 25, having a cut-off threshold on the order of 1,000 daltons, closes second ring 22.

Enclosure 12 is attached at the level of second junction ring 22, at one end of a cylindrical body 28 in which a mobile piston 30 can slide. Mobile piston 30 and the cylindrical body define an expansion chamber 31. Return means 32, for example, a spring, exert on piston 30 a pulling force tending to bring it back to its idle position. Cylindrical body 28 comprises a discharge valve 34 communicating with the outside of motor 10.

A catalyst capable of promoting a reaction of synthesis of an osmotically-active substance X from a substance Y, substance Y having a molecular mass smaller than the molecular mass of substance X, is arranged within fibers 14. The cut-off threshold of fibers 14 is set to prevent the passing of substance X and of the catalyst but allow the passing of substance Y, while the cut-off threshold of membrane 25 is set to allow the passing of substance X but to block the catalyst. In normal operation, motor 10 is placed in a surrounding medium comprising a solvent in which substance Y is dissolved.

An operating cycle of motor 10 is then carried out as follows.

FIG. 1A shows motor 10 at the beginning of a cycle. Piston 30 is in its idle position, the volume of expansion chamber 31 being minimum, and discharge valve 34 is closed. The catalyst promotes the forming of substance X from substance Y, which tends to increase the osmotic pressure inside of fiber bundle 14. The solvent of the surrounding medium penetrates into fibers 14 and into expansion chamber 31, thus displacing piston 30. The displacement of piston 30 extends spring 32, thus enabling storage of mechanical energy.

In FIG. 1B, expansion chamber 31 is shown in maximum expansion. Discharge valve 34 then opens. The pressure inside of expansion chamber 31 equalizes with the pressure of the surrounding medium. Spring 32 brings piston 30 back to its idle position by discharging, through discharge valve 34, the solvent from expansion chamber 31 into the surrounding medium. The mechanical energy stored in spring 32 is thus recovered. Valve 34 is finally closed, thus ending the motor cycle.

Piston 32 may be connected to an external element to which mechanical energy is desired to be transmitted.

As an example, substance X is a glucose polymer comprising a high number of glucose molecules, for example, dextrane, and substance Y is a glucose oligomer (which, by definition, comprises a small number of monomer units) of minimum molecular mass equal to 342 g/mol. The catalyst can then be a dextransucrase enzyme, that is, an enzyme promoting the synthesis of dextrane from a glucose oligomer.

According to the first embodiment, expansion chamber 31 is formed by a cylindrical body in which a piston slides. According to the desired use of motor 10 according to the present invention, expansion chamber 31 may be formed differently.

Figure 2A:
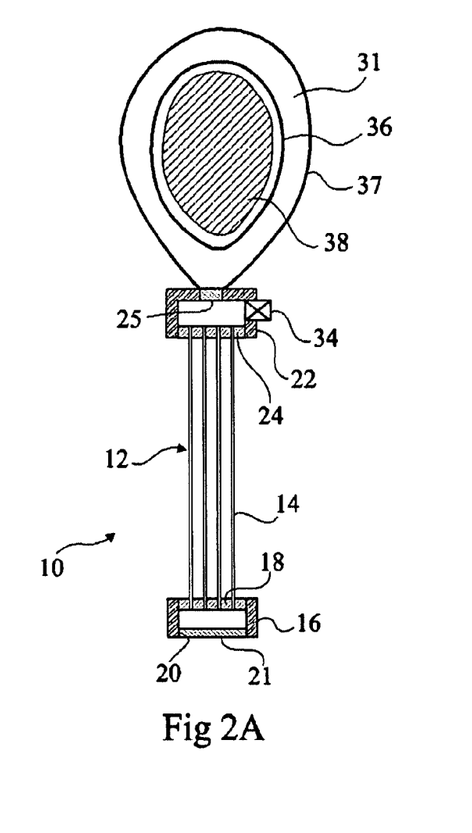
FIGS. 2A and 2B show two steps of the operation of a variation of the first embodiment of the motor according to the present invention.
Figure 2B:
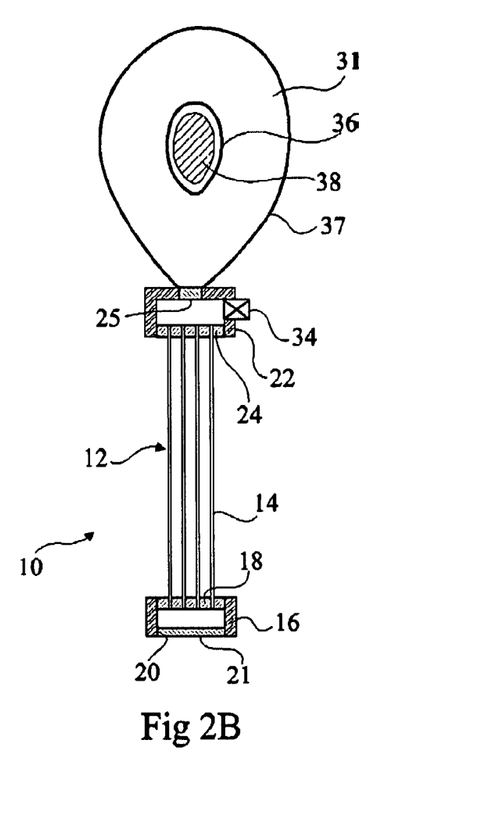

FIGS. 2A and 2B show an alternative structure of expansion chamber 31 of motor 10 of the first embodiment. According to this alternative, expansion chamber 31 corresponds to the space defined between an inner envelope 36 and an outer envelope 37, like an innertube. Inner envelope 36 is deformable and expandable and surrounds a deformable body 38. Outer envelope 37 is flexible and inextensible. It closes on inner envelope 36 and is connected to junction ring 22 of enclosure 12. Discharge valve 34 is arranged on junction ring 22. As an example, in a medical application of osmotic motor 10 according to the present invention, deformable body 38 may be the human heart and the envelopes may define expansion chambers 31 shaped as flanges surrounding the heart.

A cycle of motor 10 according to the variation of the first embodiment is the following.

FIG. 2A shows motor 10 at the beginning of a cycle. The volume of expansion chamber 31 is minimum, deformable body 38 being in maximum expansion, which may correspond to a heart in diastole. Discharge valve 34 is then closed. The catalyst promotes the forming of substance X, which causes, by osmosis, the introduction of solvent into expansion chamber 31. Inner envelope 36 deforms and compresses deformable body 38.

In FIG. 2B, deformable body 38 is in maximum compression, which may correspond to a heart in systole. On opening of discharge valve 34, the solvent is discharged from expansion chamber 31, enabling expansion of deformable body 38, which ends the cycle.

According to another variation of the present invention, the expansion chamber is formed of a resilient envelope enclosing the fibers which are arranged, for example, in a spiral, the two junction rings being tight. On synthesis of the osmotically-active substance, the fibers tend to straighten and to deform the resilient envelope. A discharge valve is provided at the level of a junction ring. On opening of the valve, the pressure inside of the fibers decreases and the envelope tends to recover its initial shape.

According to another variation of the present invention, the enclosure may be connected to the expansion chamber by a flexible duct. This enables advantageously arranging the enclosure in a surrounding medium propitious for the supply of solvent in which substance Y is dissolved, and placing the expansion chamber in a location where the mechanical energy is desired to be available. In the case of a medical application, the enclosure may be arranged in a fatty tissue, or on the vascular network. In this last case, the fibers may be arranged to form a hollow tube, leaving at its center a cylindrical space enabling the flowing of a fluid such as blood. The junction rings may be toric and placed against the wall of a blood vessel. One of the toric junction rings communicates with the expansion chamber through the flexible duct which perforates the blood vessel.

Figure 3A:
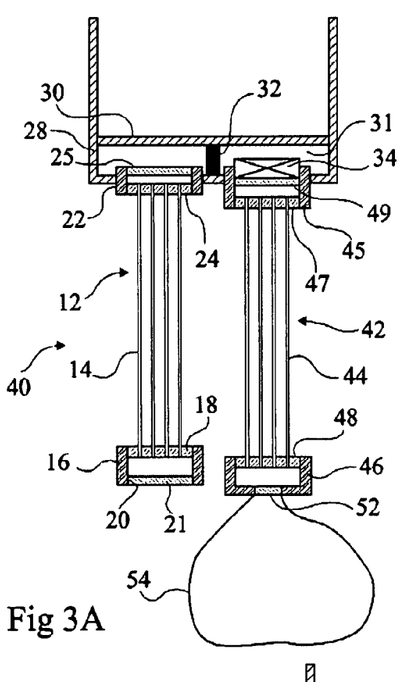
FIGS. 3A to 3C show three steps of the operation of a second embodiment of the motor according to the present invention.
Figure 3B:
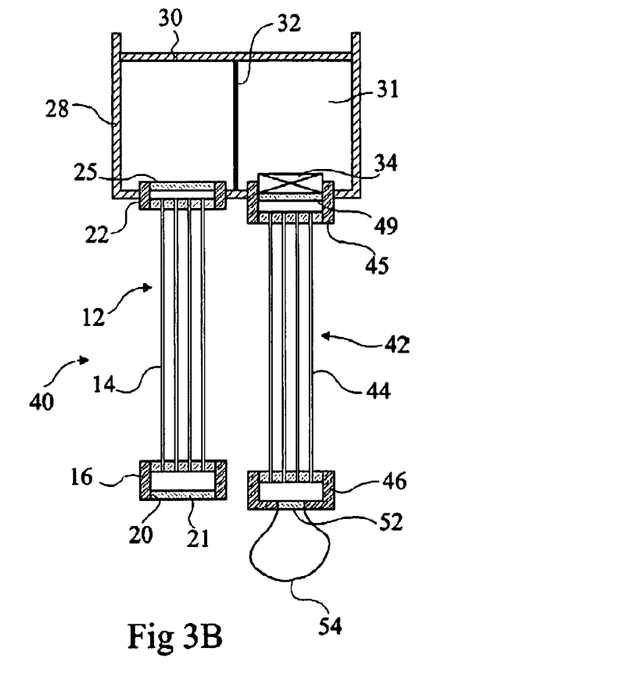
Figure 3C:
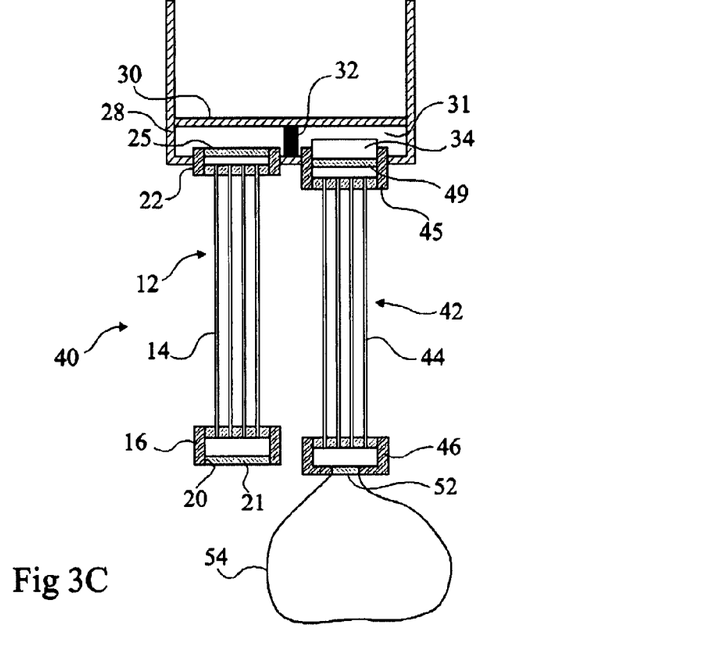

FIGS. 3A to 3C show a second embodiment of an osmotic motor according to the present invention. Motor 40 comprises the components of the motor of the first embodiment and the reference numerals associated therewith are kept.

Motor 40 comprises a first enclosure 12 of the previously-described type and a second enclosure 42. Second enclosure 42 comprises a second fiber bundle 44 maintained at its ends by junction rings 45, 46 by means of gluing areas 47, 48. Second enclosure 42 is attached on cylindrical body 28 at the level of valve 34, by junction ring 45 which comprises a membrane 49 separating expansion chamber 31 from second fibers 44. Second enclosure 42 communicates, at the level of ring 46 via a membrane 52, with a tight deformable tank 54.

A first catalyst $C_1$ promoting the forming of a substance Y from a substance X is arranged in first fiber bundle 14, so that, from an elementary particle of substance X, more than one elementary particle of substance Y is generated. A second catalyst $C_2$ promoting the forming of substance Y from substance X is arranged in second fiber bundle 44, so that, to generate one elementary particle of substance X, more than one elementary particle of substance Y is used.

According to an example, substance X is a glucose polymer comprising a high number of glucose molecules, for example, dextrane, and substance Y is a glucose oligomer. Second catalyst $C_2$ can then be a transucrase enzyme, that is, an enzyme which promotes the synthesis of dextrane from a glucose oligomer and first catalyst $C_1$ can then be a dextranase enzyme, that is, an enzyme which promotes the breakdown of dextrane into glucose or into glucose oligomers.

The walls of fiber bundle 14, 44 have a cut-off threshold lower than the molecular mass of substances X and Y. As an example, the cut-off threshold is on the order of 100 daltons when substance Y is glucose or a glucose oligomer and substance X is dextrane. Membranes 25, 49, and 52 have cut-off thresholds greater than 1,000 daltons, to let through substances X and Y and maintain the catalysts within respective fiber bundles 14, 44.

In normal operation, motor 40 is placed in a solvent. The operating cycle of osmotic motor 40 according to the present invention is the following.

FIG. 3A shows motor 40 at the beginning of the cycle. Valve 34 is closed. The concentrations in substance Y are identical in tank 54 and in expansion chamber 31, the same applying for the concentrations in substance X. In first fiber bundle 14, catalyst C1 promotes the forming of substance Y, which increases the osmotic pressure in expansion chamber 31. The solvent penetrates into first fiber bundle 14, then into expansion chamber 31, thus moving piston 30 and storing mechanical energy by the extension of spring 32. Meanwhile, in second fiber bundle 44, catalyst C2 promotes the forming of substance X, which decreases the osmotic pressure in tank 54. Tank 54 decreases in volume, without causing any work capacity since nothing opposes this decrease.

FIG. 3B shows motor 10 at the end of the previously-described step, expansion chamber 31 having a maximum volume.

Valve 34 then opens. The concentrations in substance X and in substance Y balance in fiber bundles 14, 44, expansion chamber 31, and tank 54. Similarly, the osmotic pressures balance in the different compartments. Piston 30 then moves down under the action of spring 32 to reach the position shown in FIG. 3C. Further, tank 54 expands by filling with liquid, the work required to expand tank 54 being negligible as compared with that provided by spring 32, the pressures in the surrounding medium being low as compared with those present in expansion chamber 31. Valve 34 is then closed, which ends the cycle.

The second embodiment is particularly advantageous since the exchanges between motor 40 and the surrounding medium are decreased with respect to the first embodiment. Indeed, in the first embodiment, osmotically-active substance X, for example, dextrane, is generated from substance Y, for example, a glucose oligomer, present in the solvent. Further, at the end of a motor cycle, discharge valve 34 is opened and the most part of the formed substance X is released in the surrounding medium. In the case of a medical application, the generated substance X, for example, dextrane, is released into the human body, which may be a problem. In the second embodiment, there only is a solvent transfer between motor 40 and the surrounding medium.

Figure 4A:
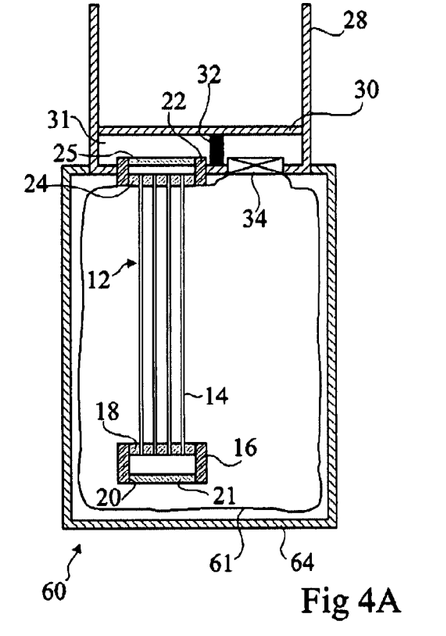
FIGS. 4A to 4C show three steps of the operation of a third embodiment of the motor according to the present invention.
Figure 4B:
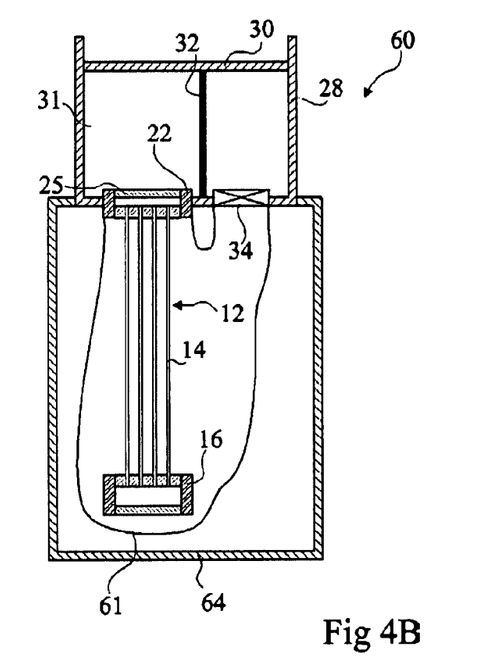
Figure 4C:
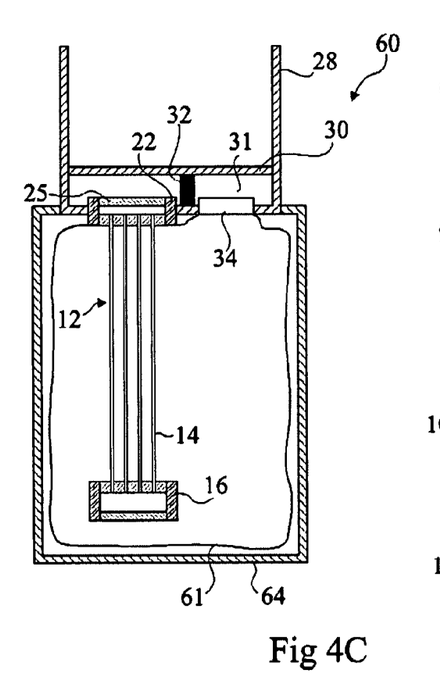

FIGS. 4A to 4C show a third embodiment of osmotic motor 60 according to the present invention. Motor 60 comprises the components of motor 10 of the first embodiment and the references numerals associated therewith are kept.

Enclosure 12 is arranged in a tight deformable envelope 61 which closes on junction ring 22 and discharge valve 34.

Envelope 61 is filled with a solvent. Envelope 61 may be arranged in a perforated rigid case 64 so as not to prevent the deformations of envelope 61.

A first catalyst $C_1$ promoting the forming of a substance Y (for example, a glucose oligomer) from a substance X (for example, dextrane), so that from one elementary particle of X, more than one elementary particle of Y are generated, is arranged in fiber bundle 14 of enclosure 12. A second catalyst $C_2$ promoting the forming of substance X from substance Y so that, to generate one elementary particle of substance X, more than one elementary particle of substance Y are used, is arranged in envelope 61.

The membranes of fiber bundle 14 have a cut-off threshold lower than the molecular mass of substances X and Y. As an example, the cut-off threshold is on the order of 100 daltons when substance Y is glucose or a glucose oligomer and substance X is dextrane.

An operating cycle of motor 60 according to the third embodiment is the following.

FIG. 4A shows motor 60 at the beginning of a cycle. Valve 34 is closed. Envelope 61 is at its maximum volume. All compartments contain a solvent in which substances X and Y are dissolved. The concentrations in X are substantially balanced between envelope 61 and expansion chamber 31. First catalyst $C_1$ promotes the forming of substance Y, which increases the osmotic pressure in bundle 14 and expansion chamber 31. Second catalyst C2 promotes the forming of substance X, thus decreasing the osmotic pressure within envelope 61. Solvent exchanges occur, the solvent passing towards fiber bundle 14 and, from there, into expansion chamber 31, causing a motion of piston 30. The piston is in ascending phase.

FIG. 4B shows motor 60 at the end of the previously-described step. The concentration in substance X is minimum inside of fiber bundle 14 and maximum inside of envelope 61. Conversely, the concentration in substance Y is maximum in fiber bundle 14 and minimum in envelope 61.

Discharge valve 34 is then opened, which directly connects up communication expansion chamber 31 and envelope 61. The pressure in expansion chamber 31 drops and return spring 32 brings piston 30 back to its initial position, discharging the solvent from expansion chamber 31 into envelope 61. The piston is said to be in descending phase. Fiber bundle 14 is thus connected up with the inside of envelope 61. The concentrations in substances X and Y equalize between the two compartments.

FIG. 4C shows motor 60 at the end of the descending phase of piston 30. Valve 34 is then closed, which ends the cycle.

A variation of the third embodiment of the osmotic motor may be used as a motor to drive the wheels of an automobile vehicle. According to this variation, the spring is suppressed and the piston is connected, for example, by a rod, to a crankshaft for driving the wheels similarly to the connection between a piston of a heat engine and the crankshaft. The propelling force corresponds to the ascending phase of the piston, that is, to the expansion phase of the expansion chamber. In descending phase, when the volume of the expansion chamber decreases, the piston only encounters a small resistance, corresponding to the flowing of the solvent through the discharge valve of the expansion chamber. Advantageously, at least two osmotic motors may be placed in parallel to drive the crankshaft so that the expansion chambers of the motors work in opposition, one of them being in expansion phase when the other is in contraction phase.

Such a motor may further be used to recover energy on braking of the vehicle. In this case, it comprises an additional valve, called a supply valve, which is arranged between the first fiber bundle and the expansion chamber. On operation of the motor to drive the wheels, the supply valve is opened so that the motor operates as described previously.

In the case of a braking, when the piston is in rising phase, the supply valve is closed and the discharge valve is opened so that the expansion chamber fills up with liquid with no significant stress. A great part of the liquid contained in the deformable envelope flows into the expansion chamber without for the concentrations in the different compartments to vary. The supply valve is then opened and the discharge valve is closed. When the piston moves down under the action of the crankshaft driven by the wheels, the liquid contained in the expansion chamber is scoured through the fiber bundle and arrives into the envelope. The work thus generated enables both slowing down the vehicle, and varying the concentrations in substances X and Y. Indeed, the osmolarity of the fiber bundle increases, while the osmolarity in the deformable chamber decreases.

Thereby, when the motor operates again as a wheel driving motor, the supply valve being open, the motor cycle resumes with a greater efficiency. Indeed, the concentration differences between the compartments will create a pressure difference due to which the cycle will be carried out faster.

Further, enclosures 12 and 42 may be formed otherwise than by a fiber bundle. They may have any shape enabling good exchange of the solutes and of the solvent on either side of the enclosure wall.

Further, valve 34 may exhibit any type of known structure. The valve openings and closings may for example be controlled by a device external to the motor, synchronously or not, or be automatically triggered by the very structure of the valve when the pressure in a motor compartment exceeds a determined value.

FIGS. 5A to 5D show a fourth embodiment of osmotic motor 80 according to the present invention. Motor 80 comprises some components of motor 60 of the third embodiment and the reference numerals associated therewith are kept.

As compared with motor 60, enclosure 12 is suppressed. A valve 82 is arranged at the level of rigid case 64 and is capable of connecting up, when opened, the content of envelope 61 with the content of an enclosure 84. A valve 86 is arranged at the level of rigid case 64 and is capable of connecting up, when opened, the content of envelope 61 with the content of an enclosure 88.

Envelope 61 contains substances U and V, dissolved in a solvent and which are likely to react in the presence of $H^+$ ions, that is, at a sufficiently acid pH, to form a substance Z. Ion $H^+$ plays a role similar to that of a catalyst of the reaction of synthesis of substance Z. The back reaction according to which substance Z is decomposed to give back substances U and V is likely to occur in the presence of ions $OH^-$, that is, at a sufficiently basic pH. Ion $OH^-$ plays a role similar to that of a catalyst of the reaction of breakdown of substance Z. Membrane 25 has a sufficiently low cut-off threshold to block substances U and V which are thus osmotically active. Valves 82, 86 are associated with membranes, not shown, which have a cut-off threshold such that they block substances U and V. According to the fourth embodiment, enclosure 84 contains an acid solution and enclosure 88 contains a basic solution.

Substances U, V, and Z must be soluble in the solvent and if possible biocompatible in the case of a medical application. As an example, substance U is a molecule comprising a primary amine function (function —$NH_2$) and substance V is a molecule comprising an aldehyde function (function —CHO). Complex-forming reactions from an amine function substance U and an aldehyde function substance V are described in works: "Advanced Organic Chemistry: Reactions, Mechanisms and Structure", third edition, J. March, John Wilez and Sons, New York (1985), pp. 796-798 and "Advanced Organic Chemistry, Part B: Reactions and Synthesis", third edition, F. A. Carey and R. J. Sundberg, Plenum Press, New-York (1990), pp. 30-31. As an example, substance U may be urea of molecular mass 60 g/mol and substance V may be vanillin of molecular mass 152 g/mol. Membrane 25 then has a 50-dalton cut-off threshold. Substance Z corresponds to a urea-vanillin complex. In this case, the urea-vanillin complex forming reaction is promoted for a pH lower than 6 while the urea-vanillin complex forming reaction is promoted for a pH on the order of 8. According to another example, compound V is a derivate of vanillin having the following formula:

where R is a carbonaceous group (R corresponding to the hydroxyl group —OH in the case of vanillin).

Expansion chamber 31 contains an osmotically active substance A, dissolved in the solvent. Membrane 25 has a sufficiently low cut-off threshold to block substance A. As an example, substance A is dextrane.

An operating cycle of motor 80 according to the fourth embodiment is the following.

Figure 5A:
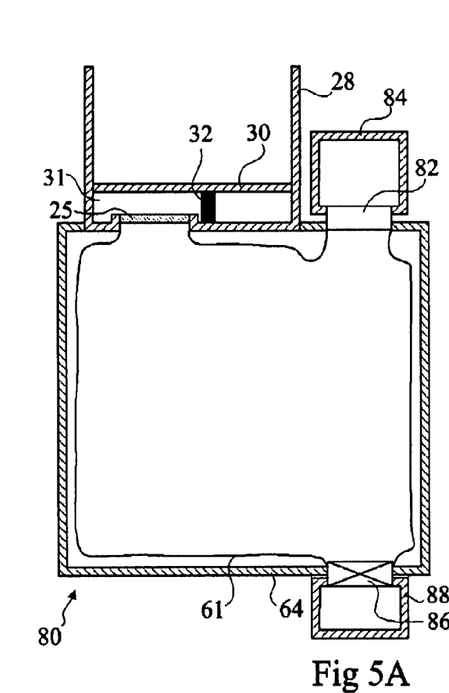
FIGS. 5A to 5D show four steps of the operation of a fourth embodiment of the motor according to the present invention.

FIG. 5A shows motor 80 at the beginning of a cycle. Envelope 61 is at its maximum volume. The concentrations in substance U and V and the concentration in substance A are initially selected so that the osmotic pressures in expansion chamber 31 and in envelope 61 balance, piston 30 remaining motionless.

Valve 86 is closed and valve 82 is then open. Ions H$^+$ spread into envelope 61, causing a decrease in the pH. When the pH in envelope 61 has decreased down to the desired value, valve 82 is closed. The reaction of forming of substance Z from substances U and V is then promoted. The osmotic pressure in envelope 61 decreases with respect to the osmotic pressure in expansion chamber 31, which does not vary. A solvent transfer thus occurs, solvent passing from envelope 61 into expansion chamber 31 through membrane 25, causing the displacement of piston 30. Piston 30 is in ascending phase.

Figure 5B:
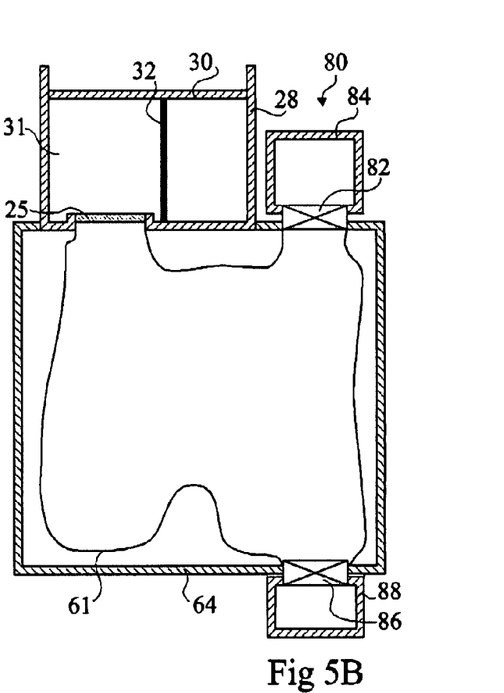

FIG. 5B shows motor 80 at the end of the ascending phase of piston 30.

Figure 5C:
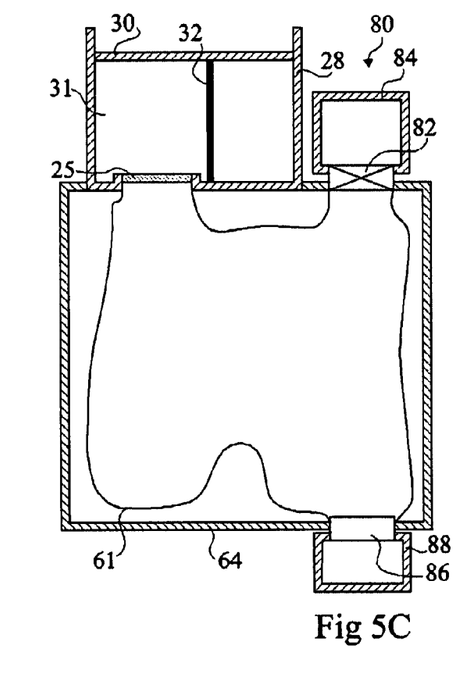

In FIG. 5C, valve 86 has been opened to connect up the content of envelope 61 with the content of enclosure 88. Ions OH$^-$ spread into envelope 61, causing a pH increase. When the pH is sufficiently basic, valve 86 is closed. The breakdown reaction of substance Z is then promoted, causing an increase in the number of osmotically active particles in envelope 61. Since the osmotic pressure increases in envelope 61, a new solvent transfer occurs, solvent passing from expansion chamber 31 to envelope 61 via membrane 25. The action of spring 32 promotes the discharge of the solvent from the expansion chamber. However, spring 32 may be omitted, with the piston being moved by suction. Piston 30 is said to be in descending phase.

Figure 5D:
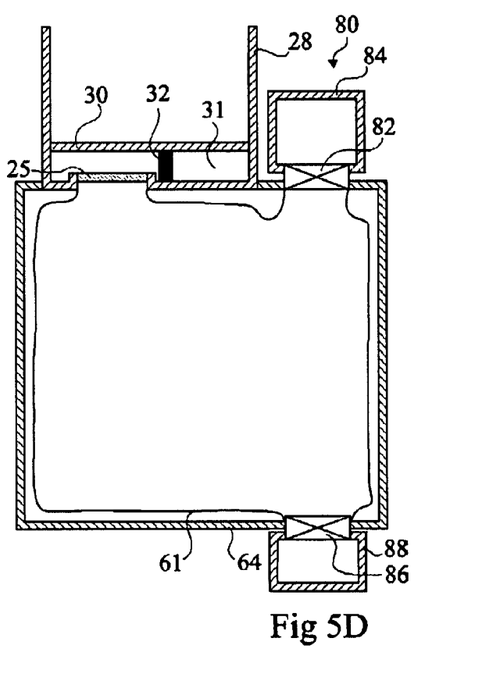

FIG. 5D shows motor 80 at the end of the descending phase of piston 30, which ends the cycle. The concentrations in substances U and V in envelope 61 are then substantially identical to the concentrations at the beginning of the cycle.

According to a variation of the fourth embodiment, membrane 25 is only impermeable to substance V but is permeable to substance U. In this case, only substances A, Z, and V are osmotically active. Substance U is free to diffuse through membrane 25 and is thus not osmotically active. In the case where substance U is urea and substance V is vanillin, membrane 25 for example has a cut-off threshold on the order of 100 daltons.

Substances U and V then have the additional feature that the forming of one particle of substance Z uses, at least in average, more than one particle of substance V. This is verified when substance U is urea and substance V is vanillin. Indeed, a molecule of the urea-vanillin complex is in average obtained from one urea molecule and more than one vanillin molecule (one or two vanillin molecules grafting on the urea according to the steric hindrance). Such a substitution reaction is described in previously mentioned reference "Advanced Organic Chemistry: Reactions, Mechanisms and Structure", third edition, J. March, John Wilez and Sons, New York (1985), p. 798.

In this case, an operating cycle of motor 80 is the following.

At the beginning of a cycle (FIG. 5A), envelope 61 is at its maximum volume. The concentration in substance V and the concentration in substance A are initially selected so that the osmotic pressures in expansion chamber 31 and in envelope 61 balance, piston 30 remaining motionless.

Valve 86 is closed and valve 82 is then opened. Ions H$^+$ spread into envelope 61, causing a pH decrease in envelope 61. The reaction of forming of substance Z from substances U and V is then promoted, substance U present in expansion chamber 31 passing into envelope 61 to take part in the reaction. Since the forming of one particle of substance Z requires more than one particle of substance V, the number of osmotically-active particles decreases in envelope 61 with respect to expansion chamber 31. The osmotic pressure in envelope 61 thus decreases with respect to the osmotic pressure in expansion chamber 31. A solvent transfer thus occurs, solvent passing from envelope 61 into expansion chamber 31 through membrane 25, causing a motion of piston 30. Piston 30 is in ascending phase.

When valve 86 is opened, valve 82 being closed (FIG. 5C), and the pH in envelope 61 becomes sufficiently basic to promote the breakdown reaction of substance Z, the number of osmotically-active particles in envelope 61 increases (even if part of substance U resulting from the breakdown diffuses into expansion chamber 31). As the osmotic pressure increases in envelope 61, a new solvent transfer occurs, solvent passing from expansion chamber 31 into envelope 61 through membrane 25.

In the previously-described examples, it is necessary to regularly refill enclosures 84, 88, respectively, with acid and basic solutions.

Figure 6:
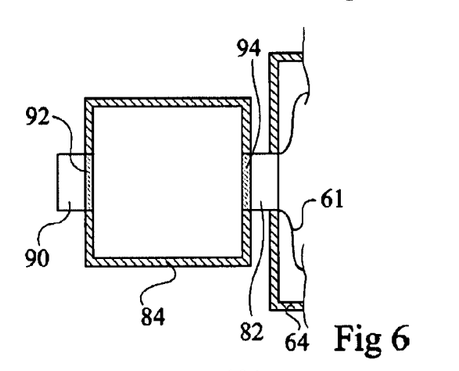
FIG. 6 shows a variation of the fourth embodiment.

FIG. 6 shows an alternative way to obtain the acid solution contained in enclosure 84 adapted to the case where enclosure 84 is bathed in a liquid surrounding medium in which glucose is dissolved, for example, a biological solvent. Enclosure 84 comprises a valve 90 capable of connecting up the content of enclosure 84 with the surrounding medium. According to such an alternative, the reaction of oxidation of glucose (noted R—COH) into gluconate (noted R—COO$^-$) according to the following reaction is promoted in enclosure 84:

R—COH+½O$_2$→RCOO$^-$+H$^+$

Such a reaction is made possible by providing in enclosure 84 a glucose oxidase enzyme. A membrane 92 between valve 90 and enclosure 84 and a membrane 94 between valve 82 and enclosure 64 are then provided, membranes 92, 94 enabling retaining the glucose oxidase enzyme, membrane 92 letting through glucose.

To obtain an acid solution in enclosure 84, valve 82 is closed and valve 90 is opened so that glucose penetrates into enclosure 84. Valve 90 is then closed. The glucose is then decomposed by generating $H^+$ ions and gluconate. The solution contained in enclosure 84 thus becomes acid and can then be used in an operating cycle of motor 80. At the next opening of valve 90, gluconate diffuses outside enclosure 84. In the case of a medical application, the releasing of gluconate into the human body is harmless since it is naturally discharged by the kidneys.

FIG. 6 shows an alternative way to obtain the acid solution contained in enclosure 84 adapted to the case where enclosure 84 is bathed in a liquid surrounding medium in which glucose is dissolved, for example, a biological solvent.

Figure 7:
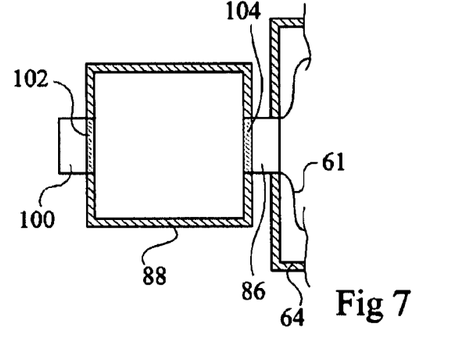
FIG. 7 shows a variation of the fourth embodiment.

FIG. 7 shows an alternative way to obtain the basic solution contained in enclosure 88 adapted to the case where enclosure 88 is bathed in a liquid surrounding medium in which urea is dissolved, for example, a biological solvent. Enclosure 88 comprises a valve 100 capable of connecting up the content of enclosure 88 with the surrounding medium. According to such a variation, the breakdown reaction of urea into ammonia and carbonic acid according to the following reaction is provided in enclosure 88:

At the physiological pH, carbonic acid dissociates into water and carbon dioxide. The ammonia will balance with water to become the ammonium ion ($NH_4^+$), thus resulting in a significant pH increase. The carbon dioxide will be naturally discharged by breathing.

Such a reaction is made possible by providing a urease enzyme in enclosure 88. A membrane 102 is then provided between valve 100 and enclosure 88 and a membrane 104 is provided between valve 86 and enclosure 64, membranes 102, 104 enabling retaining the urease enzyme, membrane 102 letting through the ammonia and the carbon dioxide.

According to another alternative embodiment, in the case of a medical application, substances U, V, and Z are such that the breakdown of substance Z which gives back substances U and V is promoted as soon as the pH is lightly basic, for example, on the order of 7.4. Enclosure 88 containing the basic solution and valve 86 are used to directly connect up the content of envelope 61 with the surrounding biological medium. Indeed, the human biological liquid naturally is at a slightly basic pH on the order of 7.4.

Of course, the present invention is likely to have various alterations, modifications, and improvements which will readily occur to those skilled in the art. In particular, for the second and third embodiments of the motor, the expansion chamber may be formed according to the described variations of the first embodiment.

Such alterations, modifications, and improvements are intended to be part of this disclosure, and are intended to be within the spirit and the scope of the present invention. Accordingly, the foregoing description is by way of example only and is not intended to be limiting. The present invention is limited only as defined in the following claims and the equivalents thereto.

What is claimed is:

1. An actuator comprising:
   an enclosure having a wall impermeable to a first solute and permeable to a solvent;
   an inanimate catalyst contained in said enclosure, said catalyst capable of promoting the transformation of at least one second solute into the first solute to vary the osmotic pressure in the enclosure; and
   a deformable chamber connected to the enclosure, said chamber being capable of increasing in volume under the action of the solvent moving from the enclosure into the chamber by osmosis or said enclosure being designed to be arranged in contact with the solvent, said chamber being capable of increasing in volume under the action of the solvent penetrating into the enclosure by osmosis
   wherein said enclosure comprises a bundle of hollow fibers, and wherein the catalyst is arranged within said fibers.

2. The actuator of claim 1, wherein said wall of the enclosure is permeable to the second solute.

3. The actuator of claim 1, wherein said wall of the enclosure is impermeable to the second solute, the catalyst being capable of promoting the transformation of a number of particles of the second solute into a greater or smaller number of particles of the first solute.

4. A motor comprising the actuator of claim 1, wherein the chamber comprises return means which oppose to the volume increase of the chamber and controllable means for lowering the osmotic pressure in the chamber.

5. The motor of claim 4, wherein said wall of the enclosure is impermeable to the second solute, the catalyst being capable of promoting the transformation of a number of particles of the second solute into a greater number of particles of the first solute, said motor further comprising an additional enclosure having a wall permeable to the solvent and impermeable to the first and second solutes and containing an additional catalyst capable of promoting the transformation of a number of particles of the first solute into a smaller number of particles of the second solute, said additional enclosure being connected to the chamber by a valve.

6. The motor of claim 4, wherein said wall of the enclosure is impermeable to the second solute, the catalyst being capable of promoting the transformation of a number of particles of the second solute into a greater number of particles of the first solute and wherein the enclosure is arranged in a deformable envelope containing the solvent and the first solute, the enclosure containing an additional catalyst capable of promoting the transformation of a number of particles of the first solute into a smaller number of particles of the second solute, the means for lowering the osmotic pressure in the chamber being a valve capable of connecting up the chamber and the envelope.

7. A motor comprising the actuator of claim 1, wherein the enclosure is at least partly deformable and is connected to the chamber at the level of the wall, the motor comprising first means for supplying the catalyst into the enclosure, and second means for supplying an additional catalyst, capable of promoting the transformation of the first solute into the at least one second solute, into the enclosure.

8. The motor of claim 7, wherein the wall is permeable to the second solute, the catalyst being capable of promoting the transformation of a number of particles of the second solute into a smaller number of particles of the first solute and the additional catalyst being capable of promoting the transformation of a number of particles of the first solute into a greater number of particles of the second solute.

9. The motor of claim 7, wherein the second solute is a compound comprising an amine function, the first solute being a complex of the second solute and of an additional solute comprising an aldehyde function, the wall being impermeable to the additional solute and wherein the catalyst is the hydrogen ion, the additional catalyst being the hydroxyl ion.

10. The motor of claim 9, wherein the first supply means comprise an additional enclosure designed to receive a solvent containing glucose, the additional enclosure containing glucose oxidase enzymes capable of promoting the oxidation of glucose to provide gluconate ions and hydrogen ions.

11. The motor of claim 9, wherein the second supply means comprise an additional enclosure designed to receive a solvent containing urea, the additional enclosure containing urease enzymes capable of promoting the oxidation of urea to provide ammonium ions and carbon dioxide.

12. The actuator of claim 1, wherein said wall is impermeable to said catalyst.

13. The actuator of claim 1, wherein the enclosure further includes:
   a first input port adapted to receive the catalyst into the enclosure; and
   a second input port adapted to receive an additional catalyst into the enclosure capable of promoting the transformation of the first solute into the at least one second solute, in the enclosure.

14. The actuator of claim 13, wherein a first valve is operatively coupled to the first input port for controlling a supply of the catalyst into the enclosure.

15. The actuator of claim 13, wherein a second valve is operatively coupled to the second input port for controlling a supply of the additional catalyst into the enclosure.

* * * * *